United States Patent [19]

Sarantakis

[11] 4,225,472
[45] Sep. 30, 1980

[54] TRUNCATED SOMATOSTATIN ANALOGS

[75] Inventor: Dimitrios Sarantakis, West Chester, Pa.

[73] Assignee: American Home Products Corporation, New York, N.Y.

[21] Appl. No.: 42,842

[22] Filed: May 29, 1979

[51] Int. Cl.³ .................. C08L 37/00; C07C 103/52; A61K 37/00
[52] U.S. Cl. ............... 260/8; 260/112.5 S; 424/177
[58] Field of Search ............ 260/112.5 S, 8; 424/177

[56] References Cited

U.S. PATENT DOCUMENTS 4,105,603  8/1978  Vale, Jr. et al. ............ 260/112.5 S

OTHER PUBLICATIONS

Vale et al., Metabolism, vol. 27, No. 9, Suppl. 1, Sep. 1978.

*Primary Examiner*—Delbert R. Phillips
*Attorney, Agent, or Firm*—Richard K. Jackson

[57] ABSTRACT

Polypeptides of the formula:

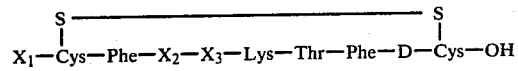

in which
 $X_1$ is hydrogen, des-amino, Ala-Gly- or Ala-D-Ala;
 $X_2$ is Trp, Leu, Met or p-Cl-Phe; and
 $X_3$ is D-Trp or 5- or 6-fluoro-D-Trp;
the linear precursor intermediates thereof or pharmaceutically acceptable salts thereof are selective inhibitors of growth hormone and glucagon release without materially altering blood serum levels of insulin.

5 Claims, No Drawings

TRUNCATED SOMATOSTATIN ANALOGS

SUMMARY OF THE INVENTION

Polypeptides of the formula:

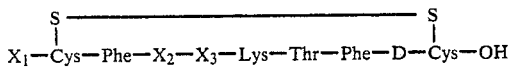

in which
X$_1$ is hydrogen, des-amino, Ala-Gly- or Ala-D-Ala-;
X$_2$ is Trp, Leu, Met or p-Cl-Phe;
X$_3$ is D-Trp or 5- or 6-fluoro-D-Trp;
the linear precursor intermediates thereof or pharmaceutically acceptable salts thereof are selective inhibitors of growth hormone and glucagon release without materially altering blood serum levels of insulin. In addition, the above-described compounds are active growth hormone suppressants for periods as long as four hours.

or ascorbic acid and the like. Acetic acid is the preferred acid.

The octapeptides selectively inhibit release of growth hormone and glucagon without materially altering blood levels of insulin. As such, they are useful in treatment of hyperglycemia in general and specifically in diabetes mellitus which is characterized by excessive glucagon secretion and deficient insulin release. Thus, for example, the postprandial hyperglycemic state in insulin-dependent diabetes may be improved through suppression of excessive glucagon by administration of the compounds of this invention with or without concomitant administration of suboptimal amounts of exogenous insulin. Likewise, the compounds of this invention are useful in the treatment of glucagon secretion by benign and malignant islet-cell tumors to obtain the normoglycemic state. In addition, the increased blood levels of growth hormone in diabetics and acromegalics can be controlled with the compounds of this invention.

The linear precursor intermediates of the cyclic octapeptides may be depicted as follows:

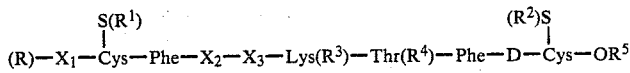

DETAILED DESCRIPTION OF THE INVENTION

In accordance with this invention there is provided a group of polypeptides of the formula:

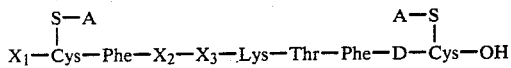

in which
X$_1$ is hydrogen, des-amino, Ala-Gly- or
X$_2$ is Trp, Leu, Met or p-Cl Phe;
X$_3$ is D-Trp or 5- or 6-fluoro-D-Trp;
and the A groups are hydrogen or a direct bond between the two sulfur atoms; or a pharmaceutically acceptable salt thereof. These compounds, while possessing the common ability to suppress growth hormone, differ from somatostatin in their selective activity toward growth hormone and glucagon without suppression of insulin, in their long term biological activity and structurally in that they omit the amino acid residues of Lys$^4$, Asn$^5$, Thr$^{12}$ and Ser$^{13}$ of somatostatin and replace Phe$^7$ with Trp, Leu, Met or P-Cl-PHe; Trp$^8$ with D-Trp or 5- or 6-fluoro-D-Trp and Cys$^{14}$ with D-Cys. In addition, the amino acid moieties appearing in 1- and 2-positions of somatostatin are either present as Ala-Gly- or they may be substituted with Ala-D-Ala, entirely omitted with or without the presence of the alpha amino substituent of Cys$^3$. Basically, the compounds of this invention may be viewed as cyclic octapeptides optionally modified N-terminally.

The preferred compounds of this invention, from the standpoint of differentiation between suppression of growth hormone, glucagon and insulin are those depicted above which contain Trp as X$_2$.

The pharmaceutically acceptable salts of the compounds of this invention are those non-toxic addition salts produced by known methods from acids conventionally employed with pharmaceuticals such as hydrochloric, hydrobromic, sulfuric, phosphoric, polyphosphoric, maleic, acetic, citric, benzoic, succinic, malonic in which
R$_1$ is hydrogen or an alpha amino protecting group;
R$^1$ and R$^2$ are hydrogen or a sulfhydryl protecting group;
R$^3$ is hydrogen or a N$^\epsilon$ protecting group of Lys;
R$^4$ is hydrogen or a hydroxyl protecting group of Thr; and
R$^5$ is hydrogen or -CH$_2$ (polystyrene resin).

These intermediates comprise the fully protected and partially protected octapeptides bound to a hydroxy methylated polystyrene resin support employed in solid phase synthesis of the polypeptide as well as the fully deprotected linear polypeptide removed from the resin support.

The protecting groups employed during preparation of the linear intermediates are conventional in solid phase polypeptide synthesis. Thus, in the above formula, the protecting group embraced in the definition of R may be formyl, trifluoroacetyl, phthalyl, p-chlorobenzyloxycarbonyl, p-nitrobenzyloxycarbonyl, tert-butyloxycarbonyl (Boc), 2,2,2-trichloroethoxycarbonyl, amyloxycarbonyl, cyclopentyloxycarbonyl, cyclohexyloxycarbonyl, trityl, etc., the preferred group being tert-butyloxycarbonyl.

Examples of the sulfhydryl protecting groups R$^1$ and R$^2$ and the hydroxyl protecting group R$^4$ of threonyl are benzyl, p-methoxybenzyl, p-chlorobenzyl, p-nitrobenzyl, trityl, benzyloxycarbonyl, p-methoxybenzyloxycarbonyl, and the like. The p-methoxybenzyl group is preferred for protection of cysteinyl sulfur while the benzyl group is preferred for the threonyl moiety.

Protecting groups for the nitrogen ($\epsilon$) atom of lysine include tosyl, benzyloxycarbonyl, 2-chlorobenzyloxycarbonyl, and tert-butyloxycarbonyl, preferably the 2-chlorobenzyloxycarbonyl group.

The support employed in the solid phase synthesis of these compounds is a chloromethylated or hydroxymethylated polystyrene resin cross-linked with divinylbenzene. These resins are prepared by known methods and are commercially available in the art.

The following examples illustrate the preparation of Cys-Phe-Trp-D-Trp-Lys-Thr-Phe-D-Cys cyclic (1–8) disulfide which is representative, in its solid phase preparation and biological activity, of the other compounds of the invention, supra.

EXAMPLE 1 tert-Butyloxycarbonyl-S-p-methoxybenzyl-L-cysteinyl-L-phenylalanyl-L-tryptophyl-D-tryptophyl-N$^\epsilon$-2-chlorobenzyloxycarbonyl-L-lysyl-O-threonyl-L-phenylalanyl-S-p-methoxybenzyl-D-cysteine hydroxymethyl polystyrene ester Chloromethylated polystyrene resin (Lab. Systems Inc.) was esterified with Boc-D-Cys(SMBzl)OH according to Gisin, Helv. Chim. Acta. 56, 1976 (1973). The polymeric ester (8 g.) was placed in a reaction vessel of a peptide synthesizer Beckman 990 A and subjected to subsequent cycles of amino group deprotection and amino acid couplings as described in Program No. 1 and Program No. 2. The last program was performed in order to insure complete coupling of each amino acid. The following amino acids were incorporated onto the resin as described above: Boc-Phe-OH, Boc-Thr(Bzl)-OH, Boc-Lys(ClCBz)-OH, Boc-D-Trp-OH, Boc-Trp-OH, Boc-Phe-OH, and Boc-Cys(SMBzl)-OH, to afford the title peptidoresin.

Program No. 1

Peptide Synthesizer-Beckman 990

1. Wash with $CH_2Cl_2 \times 3$.
2. Treat with TFA-$CH_2Cl_2$-EDT, 1:1:5% for 5 minutes.
3. Repeat (2) for 25 minutes.
4. Wash with $CH_2Cl_2 \times 4$.
5. Treat with TEA 12% in DMF for 1 minute.
6. Repeat (5) for 5 minutes.
7. Wash with $CH_2Cl_2 \times 3$.
8. Add 4 equivalents of Boc-protected amino acid and stir for 5 minutes.
9. Add 2 equivalents of 1 M-DIC solution in DMF and stir for 25 minutes.
10. Add 2 equivalents of 1 M-DIC solution in DMF and stir for 180 minutes.
11. Wash with $CH_2Cl_2 \times 3$.
12. Wash with methanol $\times 3$.
13. Wash with $CH_2Cl_2 \times 3$.

Program No. 2

Peptide Synthesizer, Beckman 990

1. Wash with $CH_2Cl_2 \times 3$.
2. Add 2 equivalents of Boc-protected amino acid and stir for 5 minutes.
3. Add 2 equivalents of 1 M-DIC solution in DMF and stir for 180 minutes.
4. Wash with DMF $\times 3$.
5. Wash with $CH_2Cl_2 \times 3$.
6. Wash with methanol $\times 3$.
7. Wash with $CH_2Cl_2 \times 3$.

EXAMPLE 2

L-Cysteinyl-L-phenylalanyl-L-tryptophyl-D-tryptophyl-L-lysyl-L-threonyl-L-phenylalanyl-D-cysteine cyclic (1–8) disulfide The peptido resin of the previous example (15 g.) was mixed with anisole (30 ml.) and treated with anhydrous HF (100 ml.) for 60 minutes in an ice-bath and under exclusion of air. The excess HF was removed as fast as possible (ca. 45 minutes) and the residue was washed with ether then taken in 20% aqueous acetic acid and added into 6 liters of degassed water. The pH of the solution was brought to 7 with dilute $NH_4OH$ and then oxidized with a solution of $K_3Fe(CN)_6$ (3 g. per 1000 ml.). The pH was adjusted to 5 with glacial acetic acid and the solution was treated with Bio-Rad AG3-X4A (100 g.) for 30 minutes and filtered. The filtrate was passed through Amberlite CG-50 (H+form) and the absorbed peptide was eluted with 50% aqueous acetic acid. The fractions containing the peptidic material were pooled and lyophilized to yield 1.1 g. of crude material. This crude product was chromatographed through a column of Sephadex G-25 (2.5 cm. $\times$ 150 cm) and eluted with 10% aqueous acetic acid. Fractions 138 to 160 (180 drops each) were pooled and lyophilized to yield the title compound, 167 mg.

TLC, silica gel G precoated glass plates $R_f$(n-BuOH-AcOH-$H_2O$-EtOAc, 1:1:1:1, v/v) 6.75.

Amino acid analysis: Thr(1) 0.98, Cys(2) 1.60, Phe(2) 2, Lys(1) 0.98, Trp(2) 1.78.

The product of the preceding examples illustrates the selective activity of the compounds of this invention for growth hormone and glucagon suppression in the following standard procedure:

Albino male rats are administered Nembutal intraperitoneally at a dose of 50 milligrams per kilogram. Fifteen minutes later a subcutaneous injection of the test compound or physiological saline (control) is administered. Ten minutes later 0.5 milliliters of arginine (300 milligrams per milliliter, pH 7.2) is injected into the heart. Five minutes after receipt of the arginine the rats are decapitated and blood is collected into trasylol-EDTA. An appropriate aliquot is assayed for growth hormone (GH), insulin, and glucagon by radioimmunoassay. The results of the assay are as follows:

| Compound | Dose µg/kg | GH ng/ml | INS µU/ml | GLUN pg/ml |
|---|---|---|---|---|
| Control | — | 488 ± 82 | 74 ± 4 | 133 ± 13 |
| Example 2 | 100 | 191 ± 60* | 69 ± 4 | 60 ± 12* |

*$p<0.05$

The duration of activity of the product of Example 2 was as follows:

| Compound | Dose µg/kg | Hours | GH ng/ml |
|---|---|---|---|
| Control | — | 2 | 369 ± 60 |
| Example 2 | 1,000 | 2 | 60 ± 6* |
| Control | — | 4 | 354 ± 68 |
| Example 2 | 1,000 | 4 | 75 ± 10* |

*$p<0.01$

As with administration of any therapeutic agent used in the treatment of diabetes mellitus, the compounds of this invention must be individualized for the patient under guidance and close control of the attending physician to reach optimum blood levels of growth hormone, insulin and glucagon. Doses for achieving the desired state vary with the condition of the patient, such as age, amount of endogenous insulin produced, the presence of glucagon secreting tumors, the route of administration, the duration of treatment, severity of the condition being treated; etc.

Thus, the compounds of this invention may be administered alone or in combination with insulin with or without carriers or excipients conventional to the route of administration selected, which may be oral, intravenous, subcutaneous, intramuscular, intranasal, intrarectally, etc. Suitable pharmaceutical compositions for application are apparent to those skilled in the art.

What is claimed is:

1. A compound of the formula

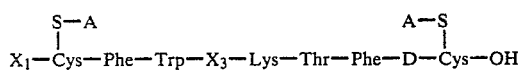

in which
X₁ is hydrogen, des-amino- Ala-Gly- or Ala-D-Ala-;
X₃ is D-Trp or 5- or 6- fluoro-D-Trp;
and the A groups are hydrogen or a direct bond between the two sulfur atoms;

or a pharmaceutically acceptable salt thereof.

2. A compound of claim 1 which is

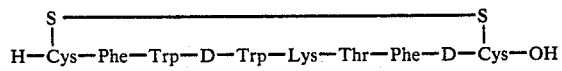

or a pharmaceutically acceptable salt thereof.

3. A compound of claim 1 which is

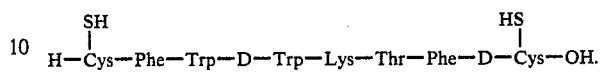

4. A compound of claim 1 which is tert-Butyloxycarbonyl-S-p-methoxybenzyl-L-cysteinyl-L-phenylalanyl-L-tryptophyl-D-tryptophyl-N-ε-2-chlorobenzyloxycarbonyl-L-lysyl-O-benzyl-L-threonyl-L-phenylalanyl-S-p-methoxybenzyl-D-cysteine hydroxymethyl polystyrene ester.

5. A compound of claim 1 which is

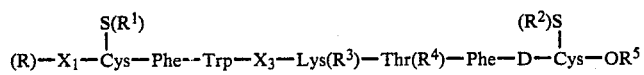

in which
R is hydrogen or an alpha amino protecting group;
R¹ and R² are hydrogen or a sulfhydryl protecting group;
R³ is hydrogen or a Nε protecting group of Lys;
R⁴ is hydrogen or a hydroxyl protecting group of Thr;
and
R⁵ is hydrogen or —CH₂(polystyrene resin).

* * * * *